(12) United States Patent
Monnet et al.

(10) Patent No.: US 8,133,168 B2
(45) Date of Patent: Mar. 13, 2012

(54) REMEDIATION OF FUNCTIONAL CARDIAC MITRAL VALVE REGURGITATION

(75) Inventors: Eric Monnet, Fort Collins, CO (US); E. Christopher Orton, Fort Collins, CO (US); Susan P. James, Bellvue, CO (US); Kyle Garrett Ordway, Arvada, CO (US); John Ordway, legal representative, Arvada, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 543 days.

(21) Appl. No.: 12/066,997

(22) PCT Filed: Sep. 1, 2006

(86) PCT No.: PCT/US2006/034389
§ 371 (c)(1),
(2), (4) Date: Jul. 17, 2009

(87) PCT Pub. No.: WO2007/035237
PCT Pub. Date: Mar. 29, 2007

(65) Prior Publication Data
US 2009/0287037 A1 Nov. 19, 2009

Related U.S. Application Data

(60) Provisional application No. 60/717,911, filed on Sep. 16, 2005.

(51) Int. Cl.
*A61N 1/362* (2006.01)

(52) U.S. Cl. .............................. 600/16; 600/17; 600/18

(58) Field of Classification Search .............. 600/16–18, 600/37; 128/897–898; 623/2.1, 2.11, 2.36, 623/2.38
See application file for complete search history.

(56) References Cited

U.S. PATENT DOCUMENTS

| 6,293,906 B1 | 9/2001 | Van den Hoek et al. |
| 6,422,990 B1 | 7/2002 | Prem |
| 2004/0260393 A1 | 12/2004 | Rahdert et al. |

FOREIGN PATENT DOCUMENTS

| WO | 2004/043265 A3 | 9/2004 |
| WO | 2004/112658 A1 | 12/2004 |

OTHER PUBLICATIONS

T. Kono et al., "Left Ventricular Shape as a Determinant of Functional Mitral Regurgitation in Patients with Severe Heart Failure Secondary to Either Coronary Artery Disease or Idiopathic Dilated Cardiomyopathy," Am. J. Cardiol. 68(4): 355-359 (1991).

(Continued)

*Primary Examiner* — Carl H Layno
*Assistant Examiner* — Paula J Stice
(74) *Attorney, Agent, or Firm* — Samuel M. Freund; Cochran Freund & Young LLC

(57) ABSTRACT

A dynamic device for reducing functional mitral regurgitation is described. The device is disposed externally to the heart and effectively acts as a splint for reducing further dilation of the heart in patients diagnosed with cardiomyopathy, and for reducing tethering of the papillary muscle on the mitral valve. The device does not require cardiopulmonary bypass for its installation since it is attached to the outside of the left ventricle, thereby reducing surgical risk, and is not exposed to the patient's blood once installed, thereby reducing the risk of thromboembolic disease.

18 Claims, 5 Drawing Sheets

OTHER PUBLICATIONS

A.C. Hueb et al., "Ventricular Remodeling and Mitral Valve Modifications in Dilated Cardiomyopathy: New Insights from Anatomic Study," J. Thorac. Cardiovasc. Surg. 124(6): 1216-1224 (2002).

R.W. Godley et al., "Incomplete Mitral Leaflet Closure in Patients with Papillary Muscle Dysfunction," Circulation 63(3): 565-571 (1981).

S.F. Bolling, "Mitral Reconstruction in Cardiomyopathy," J. Heart Valve Dis. 11, Suppl. 1:S 26-31 (2002).

K. Fukamachi et al., "Changes in Mitral Annular and Left Ventricular Dimensions and Left Ventricular Pressure-Volume Relations After Off-Pump Treatment of Mitral Regurgitation with the Coapsys Device," Eur. J. Cardiothorac.Surg. 25(3): 352-357 (2004).

S.F. Bolling et al., "Early Outcome of Mitral Valve Reconstruction in Patients with End-Stage Cardiomyopathy," J. Thorac. Cardiovasc. Surg. 109(4), pp. 676-682 (1995).

S.F. Bolling et al., "Intermediate-Term Outcome of Mitral Reconstruction in Cardiomyopathy," J. Thorac. Cardiovasc. Surg. 115(2), pp. 381-388 (1998).

M.A. Romano and S.F. Bolling, "Mitral Valve Repair as an Alternative Treatment for Heart Failure Patients," Heart Fail. Monit. 4(1), pp. 7-12 (2003).

A.M. Calafiore et al., "Mitral Valve Procedure in Dilated Cardiomyopathy: Repair or Replacement?," Ann. Thorac. Surg. 71(4), pp. 1146-1153 (2001).

A. M. Calafiore et al., "Surgical Treatment of Mitral Valve Regurgitation in Dilated Cardiomyopathy," Heart Surg. Forum, 7(1), pp. E67-E71 (2004).

N.D. Radovanovic et al., "Surgical Treatment of Heart Failure in Patients with Primary and Ischemic Dilated Cardiomyopathy," Heart Surg. Forum 6(5), pp. 320-327 (2003).

C.G. Duran and J.L. Ubago, "Clinical and Hemodynamic Performance of a Totally Flexible Prosthetic Ring for Atrioventricular Valve Reconstruction," Ann. Thorac. Surg. 22(5), pp. 458-463 (1976).

Z.A. Szalay et al., "Mitral Annuloplasty in Patients with Ischemic Versus Dilated Cardiomyopathy," Eur. J. Cardiothorac. Surg. 23(4), pp. 567-572 (2003).

P. Dagum et al., "Three-Dimensional Geometric Comparison of Partial and Complete Flexible Mitral Annuloplasty Rings," J. Thorac. Cardiovasc. Surg. 122(4), pp. 665-673 (2001).

G. Gatti et al., "Mitral Valve Surgery for Mitral Regurgitation in Patients with Advanced Dilated Cardiomyopathy," Ital. Heart J. 4(1), pp. 29-34 (2003).

E.S. Bishay et al., "Mitral Valve Surgery in Patients with Severe Left Ventricular Dysfunction," Eur. J. Cardiothorac. Surg. 17(3), pp. 213-221 (2000).

A. Carpentier et al., "Dynamic Cardiomyoplasty at Seven Years," J. Thorac. Cardiovasc. Surg. 106, pp. 42-54 (1993).

J. H. Oh et al., "The Effects of Prosthetic Cardiac Binding and Adynamic Cardiomyoplasty in a Model of Dilated Cardiomyopathy," J. Thorac. Cardiovasc. Surg. 116, pp. 148-153 (1998).

International Search Report for PCT/US06/34389, International Searching Authority, Mar. 13, 2007, pp. 1-6.

REMEDIATION OF FUNCTIONAL CARDIAC MITRAL VALVE REGURGITATION

CROSS-REFERENCE

This application is the U.S. National Stage patent application of International Application No. PCT/US2006/034389, filed on Sep. 1, 2006, which claims the benefit under 35 U.S.C. section 119 (e) of U.S. Provisional Application 60/717,911 filed on Sep. 16, 2005, both of which are hereby incorporated by reference herein.

FIELD OF THE INVENTION

The present invention relates generally to chronic cardiomyopathy and, more particularly to the use of a dynamic device, external to the heart, for remediation of functional mitral valve regurgitation.

BACKGROUND OF THE INVENTION

Functional mitral regurgitation is believed to result from the absence of coaptation of the mitral valve leaflets without any mitral valve disease. It is a risk factor of dilated cardiomyopathy and ischemic cardiomyopathy as a consequence of ventricular remodeling and dilation of the valvular annulus, and/or papillary muscle dysfunction. Modification of the geometry of the left ventricle by the tethering force of the papillary muscle is believed to be a significant cause of mitral valve regurgitation during dilated cardiomyopathy, while papillary and left ventricular dysfunction appears to be a significant cause of mitral valve regurgitation when myocardial ischemia is present (See e.g., T. Kono et al., "Left ventricular shape as a determinant of functional mitral regurgitation in patients with severe heart failure secondary to either coronary artery disease or idiopathic dilated cardiomyopathy" *Am. J. Cardiol.* 68(4):355-359 (1991); A. C. Hueb et al., "Ventricular remodeling and mitral valve modifications in dilated cardiomyopathy: new insights from anatomic study" *J. Thorac. Cardiovasc. Surg.* 124(6):1216-1224 (2002); and R. W. Godley et al., "Incomplete mitral leaflet closure in patients with papillary muscle dysfunction" *Circulation* 63(3):565-571 (1981).). Ventricular dilation increases the tethering on the chordea and changes the papillary angle, resulting in a reduction of the area of coaptation of the valve leaflet. With further dilation of the left ventricle the valve leaflets cannot make effective contact and regurgitation occurs (See, e.g., S. F. Bolling, "Mitral reconstruction in cardiomyopathy" *J. Heart Valve Dis.* 11, Suppl. 1:S 26-31 (2002).).

Coaptation of the mitral valve leaflet must be reestablished to prevent deterioration of cardiac function. Mitral valve annuloplasty using an undersized ring to provide leaflet coaptation in patients with cardiomyopathy has been shown to provide improved survival and good palliation of dilated cardiomyopathy and ischemic cardiomyopathy. However, this procedure requires cardiopulmonary bypass which results in a high mortality rate for patients. Additionally, undersized annuloplasty does not treat the underlying problem of tethering on the mitral valve and sphericity of the heart, and places the patient at greater risk for further heart dilation and deterioration of cardiac function.

In "Changes in mitral annular and left ventricular dimensions and left ventricular pressure-volume relations after off-pump treatment of mitral regurgitation with the Coapsys device" by K. Fukamachi et al., *Eur. J. Cardiothorac. Surg.* 25(3):352-357 (2004), the authors describe a device which places two pads against the left ventricle underneath the mitral valve annulus, using a string which is passed through the left ventricular chamber connecting the two pads. Since the device is in contact with blood within the heart, risk of thromboembolism is significantly increased. A similar device is described in "Tensioning device and system for treating mitral valve regurgitation" by Elliot Bloom et al., PCT International Publication No. WO 2004/112658 A1 (29 Dec. 2004). Again, the tensioning device is in contact with the blood within the heart.

In U.S. Pat. No. 6,293,906 for "Delivery Of Cardiac Constraint Jacket" by John C. Van den Hoek and Jody L. Rivers, a cardiac constraint jacket is described which is formed of flexible material defining a volume between an open upper end and a lower end, and adapted for an apex of a patient's heart to be inserted into the volume through the open upper end and for the jacket to be slipped over the heart. The jacket can be used in early stages of congestive heart disease. For patients having heart enlargement as a result of viral infection, the jacket permits constraint of the heart for a sufficient time to permit the viral infection to pass. In addition to preventing further heart enlargement, the jacket treats valvular disorders by constraining circumferential enlargement of the valvular annulus and deformation of the ventricular walls. Once placed on the heart, the jacket is adjusted to a snug fit on the heart during diastole.

International Publication No. WO 2004/043265 for "Devices And Methods For Heart Valve Treatment" by Robert M. Vidlund et al. describes methods and devices for improving the function of mitral valves by positioning an implantable device outside and adjacent the heart wall such that the device alters the shape of the heart wall acting on the valve by applying an inward force and/or by circumferential shortening, and may increase coaption of the leaflets to reduce regurgitation. In the General Description of Exemplary Implant Devices section of this patent application, an implantable device including two or more anchor ends with an interconnecting member connected therebetween is described. The anchor ends may be configured to permanently or releasably attach to the outside of the heart wall. The interconnecting member may be selectively tightened or loosened to correspondingly affect the tension between the anchor ends. A protrusion may be connected to the interconnecting member between the anchor ends, or the anchor ends may be utilized without the use of a protrusion. With or without the protrusion, the interconnecting member may be generally flexible to conform to the outer surface of the heart.

Accordingly, it is an object of the present invention to provide a device for reducing mitral valve regurgitation resulting from cardiac dilation and/or tethering of the papillary muscle.

Another object of the invention is to provide a device for reducing cardiac functional mitral valve regurgitation resulting from cardiac dilation and/or tethering by the papillary muscle where the device is not in contact with blood of the patient after placement in the body.

Still another object of the invention is to provide device for reducing cardiac functional mitral valve regurgitation resulting from cardiac dilation and/or tethering of the papillary muscle which does not require cardiopulmonary bypass for installation thereof.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus adapted for external attachment to the left ventricle of a heart for remediating mitral valve regurgitation, hereof, includes: a U-shaped member having a planar portion, a first leg having at least one first hole therethrough, and a second leg parallel to the first leg having at least one second hole therethrough, the first leg having a portion thereof directed out of the planar portion at a first chosen angle and the second leg having a portion thereof directed out of the planar portion at a second chosen angle on the same side thereof as the out-of-plane portion of the first leg; a first rod having an enlarged portion at one end thereof adapted to slidably move in one of the at least one holes through the first leg; a second rod having an enlarged portion at one end thereof adapted to slidably move in one of the at least one second holes through the second leg; a first spring disposed between the end of the first rod bearing the enlarged portion and the first leg, for spring-loading the first rod; and a second spring disposed between the end of the second rod bearing the enlarged portion and the second leg, for spring-loading the second rod, wherein the enlarged portion of the first rod and the enlarged portion of the second rod provide a force against the left ventricle effective for reducing mitral valve regurgitation when the apparatus is attached to the left ventricle of a heart.

Benefits and advantages of the present invention include, but are not limited to, providing a device for reducing mitral valve regurgitation resulting from cardiac dilation and/or tethering of the papillary muscle, where the device is not in contact with blood of the patient after placement in contact with the left ventricle of the heart, and does not require cardiopulmonary bypass for its installation.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 2A is a projection view of the apparatus illustrated in FIGS. 1A-1C hereof attached to a heart, while

DETAILED DESCRIPTION OF THE INVENTION

Figure 1A:
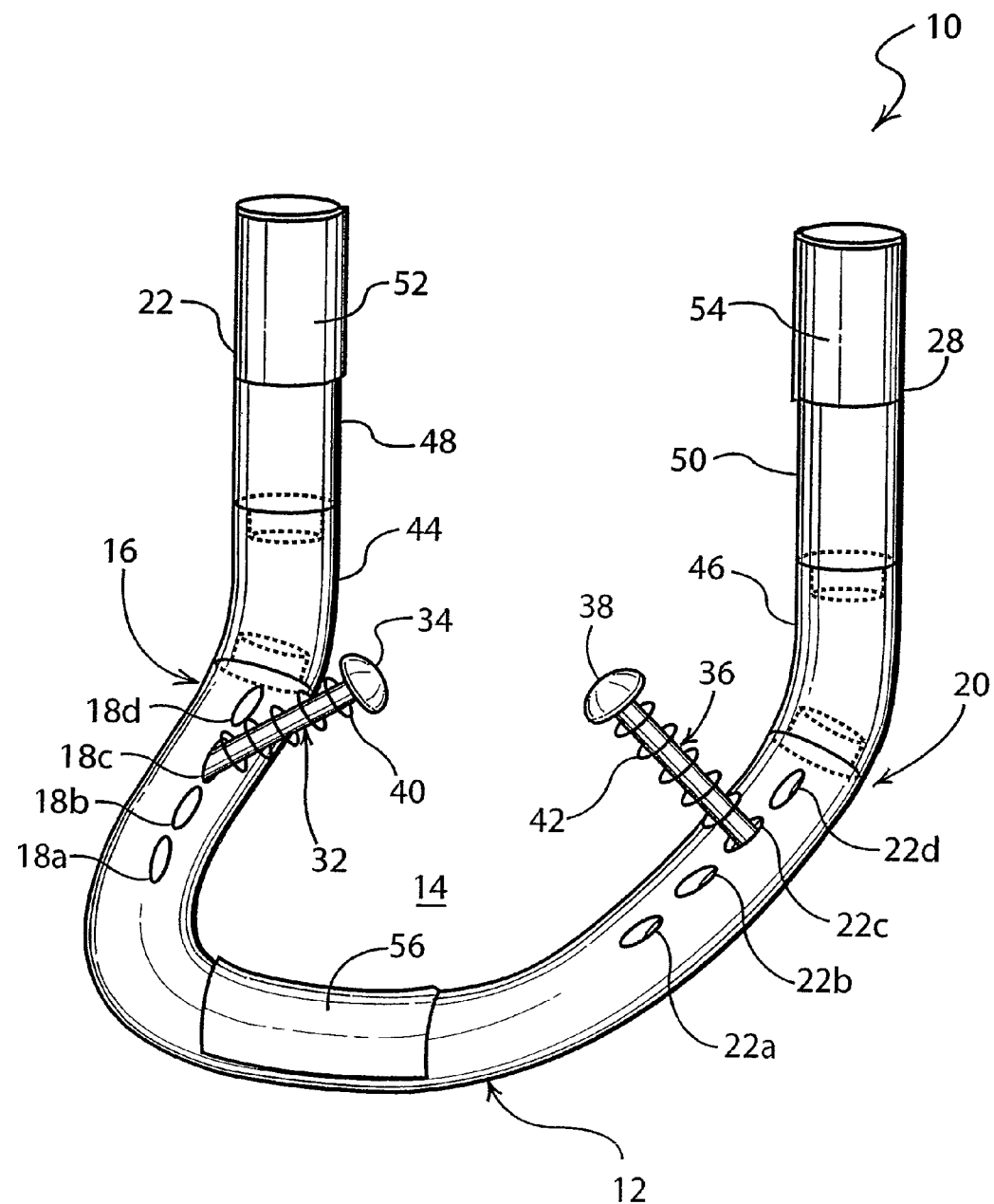
FIG. 1A is a projection view of the present apparatus for reducing functional mitral valve regurgitation.

Briefly, the present invention includes a dynamic device for splinting a heart and disposed externally thereto for preventing further dilation of the heart in patients diagnosed with cardiomyopathy. As used herein, the term "patients" includes humans, dogs, and other animals. The invention further finds applicability for reducing tethering of the papillary muscle on the mitral valve, thereby reducing functional mitral regurgitation. Cardiopulmonary bypass is not required for installation of the device since it is attached to the outside of the left ventricle, thereby reducing surgical risk, and it is not exposed to the patient's blood once installed, thereby reducing the risk of thromboembolic disease. The device can be custom fitted for each patient at the time of surgery to accommodate different heart sizes, and has a passive spring mechanism that provides heart splinting and which will return energy generated during diastole to the heart during systole. The force exerted by the spring mechanism can be adapted to optimize the cardiac function for each patient at the time of surgery by selecting appropriate spring constants. No external energy source is required.

The present device may be combined with an external procedure for the mitral valve annulus (see, e.g., S. F. Bolling, "Mitral reconstruction in cardiomyopathy" *J. Heart Valve Dis.* 11 Suppl. 1, pages S 26-31 (2002); S. F. Bolling et al., "Early outcome of mitral valve reconstruction in patients with end-stage cardiomyopathy" *J. Thorac. Cardiovasc. Surg.* 109 (4), pages 676-682 (1995); S. F. Bolling et al., "Intermediate-term outcome of mitral reconstruction in cardiomyopathy" *J. Thorac. Cardiovasc. Surg.* 115(2), pages 381-386; discussion on pages 387-388 (1998); M. A. Romano and S. F. Bolling, "Mitral valve repair as an alternative treatment for heart failure patients" *Heart Fail. Monit.* 4(1), pages 7-12 (2003); A. M. Calafiore et al., "Mitral valve procedure in dilated cardiomyopathy: repair or replacement?" *Ann. Thorac. Surg.* 71(4), pages 1146-1152 (2001) and discussion pages 1152-1143; A. M. Calafiore et al., "Surgical Treatment of Mitral Valve Regurgitation in Dilated Cardiomyopathy" *Heart Surg. Forum.* 7(1), pages 21-25 (2004); N. D. Radovanovic et al., "Surgical treatment of heart failure in patients with primary and ischemic dilated cardiomyopathy" *Heart Surg. Forum* 6(5), pages 320-327 (2003); C. G. Duran and J. L. Ubago, "Clinical and hemodynamic performance of a totally flexible prosthetic ring for atrioventricular valve reconstruction" *Ann. Thorac. Surg.* 22(5), pages 458-463 (1976); Z. A. Szalay et al., "Mitral annuloplasty in patients with ischemic versus dilated cardiomyopathy" *Eur. J. Cardiothorac. Surg.* 23(4), pages 567-572 (2003); P. Dagum et al., "Three-dimensional geometric comparison of partial and complete flexible mitral annuloplasty rings" *J. Thorac. Cardiovasc. Surg.* 122(4), pages 665-673 (2001); G. Gatti et al., "Mitral valve surgery for mitral regurgitation in patients with advanced dilated cardiomyopathy" *Ital. Heart J.* 4(1), pages 29-34 (2003); and E. S. Bishay et al., "Mitral valve surgery in patients with severe left ventricular dysfunction" *Eur. J. Cardiothorac. Surg.* 17(3), pages 213-221 (2000)) to improve coaptation of the mitral valve leaflets. The present device is expected to provide a support to the heart similar to that provided by dynamic cardiomyoplasty (see, e.g., A. Carpentier et al., "Dynamic cardiomyoplasty at seven years" *J. Thorac. Cardiovasc. Surg.* 106, pages 42-54 (1993); and J. H. Oh et al., "The effects of prosthetic cardiac binding and adynamic cardiomyoplasty in a model of dilated cardiomyopathy" *J. Thorac. Cardiovasc. Surg.* 116, pages 148-153 (1998)), but with the additional specific treatment of mitral regurgitation by reducing papillary tethering.

In-vitro evaluation of an aluminum embodiment of the present invention having fewer adjustable parts on a normal canine heart has demonstrated that application of forces at the level of the papillary muscle in the direction of the mitral valve reduces tethering of the mitral valve leaflet, and the distance between the two papillary muscles was found to be reduced from 1.3 cm to 0.96 cm, or 26%.

As will be described in the EXAMPLE hereinbelow, a stainless steel embodiment of the present device, once installed in-vivo, was found not to interfere with cardiac function including myocardial perfusion, systole and diastole, since currently employed devices, which are designed to reduce cardiac dilation by forming a passive, substantially rigid girdle (adynamic cardiomyoplasty) around the epicardium, have not been found to interfere with diastole. In use, the device of the present invention has been applied principally to the left ventricle (not the entire epicardium), thereby reducing interference with diastole. As stated hereinabove, the spring-loading feature of the present invention is expected to assist the heart during systole.

One procedure for attaching the present device to the left ventricle includes intercostal thoracotomy with the patient being placed in right lateral recumbency for surgery. A fifth left intercostal sternotomy may be performed to obtain access to the left ventricle, the left atrio-ventricular groove, the ascending and descending aorta, and the left atrium. The pericardium may be incised from the apex of the heart toward the cranial and caudal border of the heart. The device was applied to the ventricle in contact with the epicardium such that the left ventricular end diastolic pressure is increased between 0% and 10% from a measured baseline pressure. Cardiac function may be evaluated by echocardiography, as an example, and left and right heart catheterization will be performed before surgery and subsequent thereto. For example, a Swan Ganz catheter may be used for right heart catheterization to determine pulmonary arterial pressures, right ventricular pressures, right atrial pressure, pulmonary artery wedge pressure and cardiac output before and after placement of the device, while a microtip Millar Impedance catheter may be used for left heart catheterization to determine, left ventricular systolic pressure, left ventricular end diastolic pressure, left ventricular volume, dp/dt, dv/dt, end systolic and diastolic pressure volume relationship, E max, external or stroke work (EW), tau, and beta (coefficient of chamber stiffness) before and after placement of the device.

Reference will now be made in detail to the present embodiments of the invention, examples of which are illustrated in the accompanying drawings. Similar or identical structure will be identified using identical callouts. Turning now to FIG. 1A hereof, a projection view of an embodiment of present apparatus, 10, for reducing functional mitral valve regurgitation is shown. U-shaped member, 12, having a planar portion, 14, a first leg, 16, having at least one hole therethrough, 18a-18d, and a second leg, 20, parallel to the first leg having at least one hole therethrough, 22a-22d, leg 16 having a portion, 22, thereof directed out of planar portion, 14, at a first chosen angle, 26 ($\theta_1$, illustrated in FIG. 1B hereof), and leg 20 having a portion, 28, thereof directed out of the planar portion at a second chosen angle, 30 ($\theta_2$, illustrated in FIG. 1B hereof, and shown to be the same angle as first chosen angle 26), on the same side thereof as the out-of-plane portion of the first leg. Holes, 18a-18d and 22a-22d, permit the most effective support location to be chosen during the installation of the device. Clearly, a greater or smaller number of holes can be used. U-shaped member 12 was designed to withstand the static, dynamic and fatigue loads of the heart while being small in size; stainless steel (316L) tubing may be used to fabricate U-shaped member 12 because of its biocompatibility resistance to corrosion and fatigue. A safety factor of three for mechanical failure was designed into the present device. Other materials are anticipated as being useful as long as they meet the mechanical strength, biocompatibility, corrosion and fatigue resistance requirements of the present invention, and can survive rigorous sterilizations. The device may include solid members or tubes, or mixtures thereof.

Returning to FIG. 1A, apparatus 10 further includes first rod, 32, having an enlarged portion, 34, at one end thereof adapted to slidably move in one of the at least one holes through leg 16; a second rod, 36, having an enlarged portion, 38, at one end thereof adapted to slidably move in one of the at least one second holes through leg 20; a first spring, 40, disposed between the enlarged portion of rod 32 and leg 16 for spring-loading rod 32; and a second spring, 42, disposed between the enlarged portion of rod 36 and leg 20, for spring-loading rod 36. Legs 16 and 20 can be formed from bent portions, 44 and 46, and straight portions, 48 and 50, respectively, which are screwed together or otherwise interlocked and fixed using a bayonet design and set screws, as examples. This permits accommodation of the present apparatus to different heart sizes and shapes during surgery. Springs 40 and 42 may be chosen during surgery from a group of springs. The adjustable height of the spring arm and choice of spring constants will allow intra-operative adjustment of the amount of pressure needed to be applied to move the papillary muscle toward the mitral valve annulus.

Many materials are anticipated as being useful for the fabrication of the various components of the present invention. As examples, stainless steel, titanium alloys, zirconium alloys, magnesium alloys, cobalt-chrome alloys, fiber reinforced composites, particulate reinforced composites, polymer resins, and polymer/metal constructs, as examples. It is also anticipated that coatings that enhance the biocompatibility of some of these materials may be utilized. For example, springs 40 and 42 may be coated to prevent fibrous tissue growth thereon, thereby reducing the likelihood that these springs will be overgrown after implantation of the device, and lose their effectiveness.

Suturing locations bearing Teflon pledgets, 52, 54, and 56, attached to legs 16 and 20, and U-shaped member 12, respectively, are adapted for suturing to the heart. Other methods for securing apparatus 10 to the left ventricle of a heart are also anticipated, as are other materials for the pledgets. Straight portions 48 and 50 may be enlarged or broadened in the region of pledgets 52 and 54 in order to reduce the likelihood that the heart is punctured by these rods or tubes.

Figure 1B:
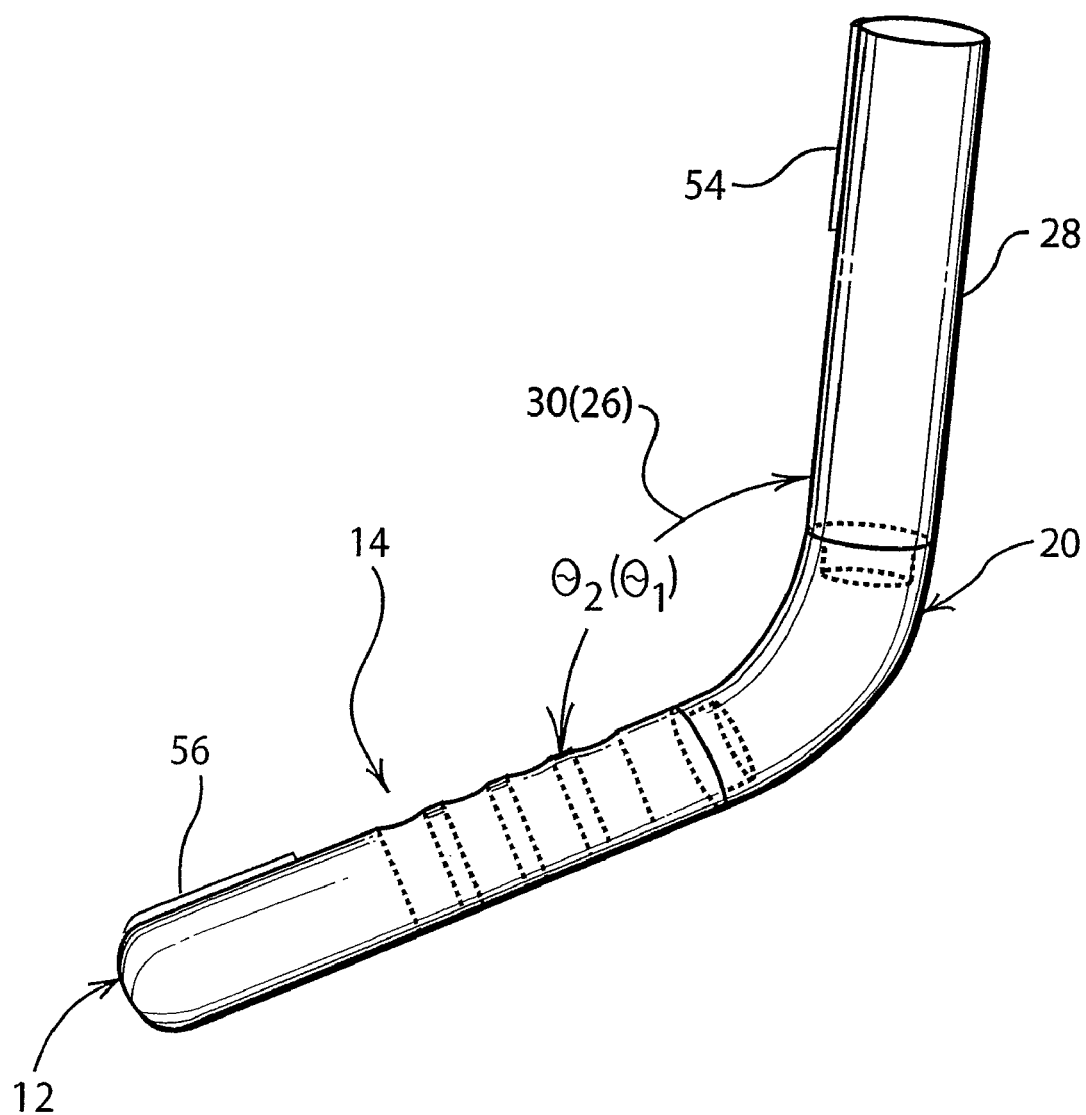
FIG. 1B shows a side view of the apparatus having the rods removed for clarity.

FIG. 1B shows a side view of the present apparatus, illustrating second chosen angle 30 (26) between that portion 28 of leg 20 which is directed out of the plane of planar portion 14 of U-shaped member 12 and the plane. Second chosen angle 30 ($\theta_2$) is shown to be equal to first chosen angle 26 ($\theta_1$), which will generally be the case; however, there may be instances in which the two angles are different. The range of angles $\theta_1$ and $\theta_2$ may be between 120° and 150°.

Figure 1C:
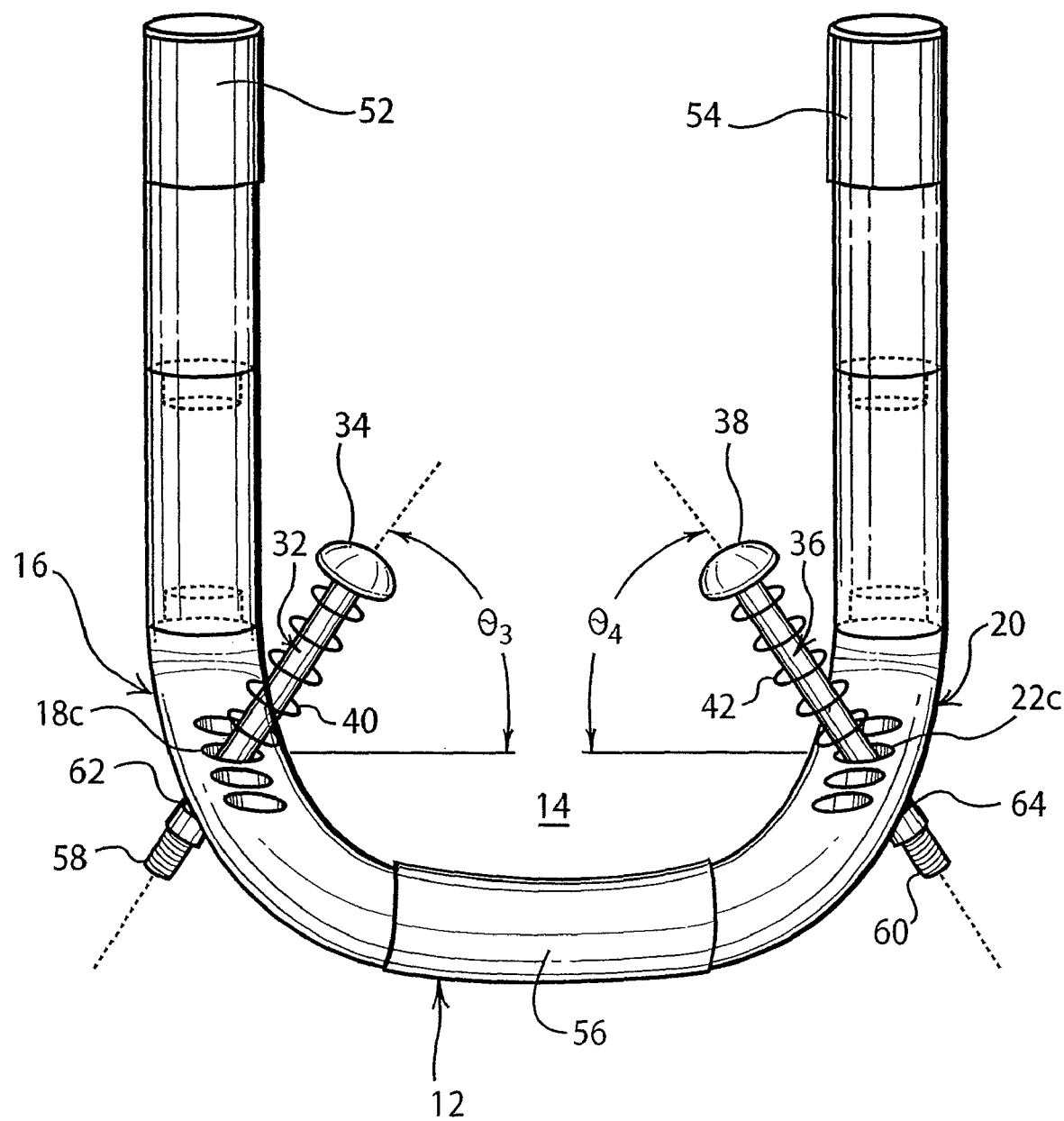
FIG. 1C shows a front view of thereof.

FIG. 1C shows a front view of the present apparatus, illustrating the angles rods 32 and 36 make with the planar portion 14 of U-shaped member 12 ($\theta_3$ and $\theta_4$, respectively) as a result of the orientation of holes 18a-18d and 22a-22d, respectively. Angles $\theta_3$ and $\theta_4$ may be different in magnitude; in most applications, however, it is anticipated that these angles will be the same and have a range between 35° and 55°. Shown also are threaded portions, 58 and 60, of rods 32 and 38, respectively, and nuts, 62 and 64, for holding rods 32 and 38 in holes 18c and 22c, respectively, against the action of springs 40 and 42, respectively.

Rods 32 and 36 provide focal support to the papillary muscle, as will be discussed in more detail hereinbelow; separate rods allow for more precise and adjustable positioning. Finite element analysis was used to design U-shaped member 12 and springs 40 and 42. Springs 40 and 42 may be designed to approximate the elasticity of the heart tissue and to reach full compression at the maximum force output of the heart, thereby reducing shock to the heart, providing a prescribed displacement for the heart, and returning a significant portion of the compression energy thereto. Plastic or other material spacers may be adapted to fit on rods 32 and 36 between first leg 16 and second leg 20 and springs 40 and 42, respectively, to adjust the spring-loading of rods 32 and 36 (not shown in the Figures). The spacers may be slidably attached to rods 32 and 36.

Figure 2A:
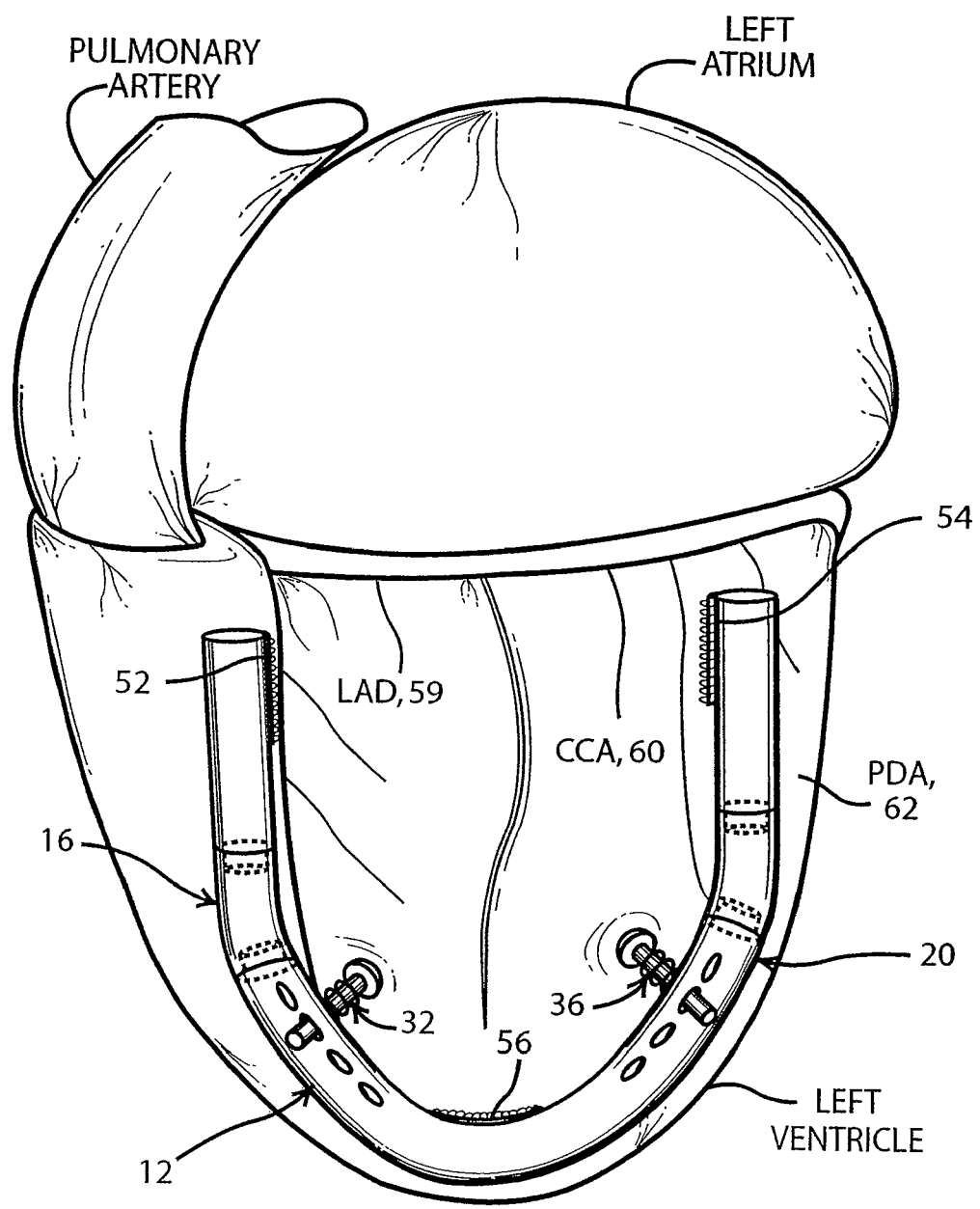

Apparatus 10 may be installed using a mattress suture with 2-0 polypropylene mounted on pledget 52 located caudal to left anterior descending coronary artery (LAD), 59, and ventral to circumflex coronary artery (CCA), 60, as shown in FIG. 2A. Another mattress suture with 2-0 polypropylene mounted on pledget 54 may be located caudal to left posterior descending artery (PDA), 62, and ventral to CCA 60. These two sutures may pierce the pads or otherwise be attached to the legs of the device. A third mattress suture with 2-0 polypropylene mounted on pledget 56 may be located at the apex of the heart with sutures piercing the pad or otherwise attached to U-shaped member 12.

Figure 2B:
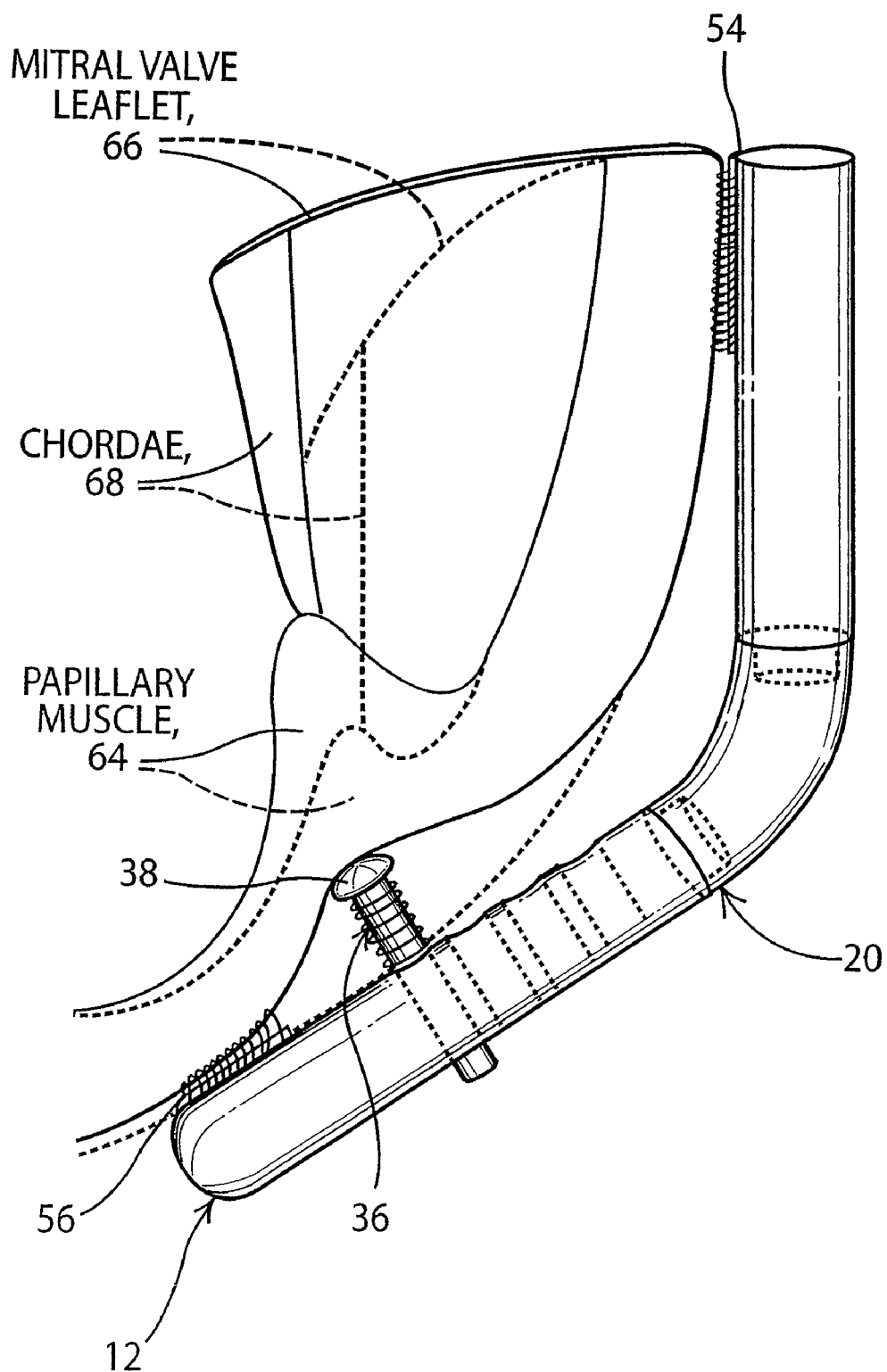
FIG. 2B is a side view thereof

After positioning device 10 on the left ventricle, spring-loaded rods 32 and 36 are installed. As stated, particular holes 18*a*-18*d* and 22*a*-22*d* are chosen to accommodate the individual heart, with suitable spring pressure being applied such that the papillary muscle is moved toward the mitral valve annulus, and the left ventricular diastolic pressure is increased by about 10% from a measured baseline value. The dashed structural elements shown in FIG. 2B hereof illustrate the result of distended papillary muscle, 64, in displacing mitral valve leaflet, 66, from its normal location through the action of chordae, 68. The present device will restore the mitral valve leaflets to more effective locations by rods 32 and 36 working to displace both papillary muscles to more normal positions (solid structure in FIG. 2B), thereby permitting the mitral valve to function more optimally. Capillary blood flow may be measured in the left atrium by means of a pressure-measuring catheter before and after application of the device to the heart, and blood flow may be measured in both papillary muscles underneath the device and in the middle of the posterior left ventricular wall.

Having generally described the present method, more details thereof are presented in the following EXAMPLE.

EXAMPLE

The device of the present invention was surgically implanted in 4 healthy dogs without heart failure. The stainless steel (311L) device was disposed on the left ventricle, and the support rods were placed against the base of the papillary muscles. The surgery was well tolerated by the dogs, with normal recovery and only minor arrhythmias post operatively which resolved after 2 weeks of treatment. No pleural effusion or infection was observed. There was no negative effect on cardiac function or myocardial blood flow after 10 weeks, and no ischemia was observed in the myocardium.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus adapted for external attachment to a left ventricle of a heart for remediating mitral valve regurgitation, which comprises in combination:

(a) a U-shaped member having a planar portion, a first leg having at least one first hole therethrough, and a second leg parallel to the first leg having at least one second hole therethrough, the first leg having a portion thereof directed out of the planar portion at a first chosen angle and the second leg having a portion thereof directed out of the planar portion at a second chosen angle on the same side thereof as the out-of-plane portion of the first leg;

(b) a first rod having an enlarged portion at one end thereof adapted to slidably move in one of the at least one holes through said first leg;

(c) a second rod having an enlarged portion at one end thereof adapted to slidably move in one of the at least one second holes through said second leg;

(d) a first spring disposed between the end of said first rod bearing the enlarged portion and said first leg, configured to spring-load said first rod; and (e) a second spring disposed between the end of said second rod bearing the enlarged portion and said second leg, configured to spring-load said second rod, wherein the enlarged portion of said first rod and the enlarged portion of said second rod provide a force against the left ventricle in an amount effective to reduce mitral valve regurgitation when said apparatus is attached to the left ventricle of a heart.

2. The apparatus of claim 1, wherein the enlarged portion of said first rod and the enlarged portion of said second rod are angled toward each other when said first rod is disposed in one of the at least one first holes through the first leg and said second rod is disposed in one of the at least one second holes through the second leg.

3. The apparatus of claim 1, wherein the first chosen angle is equal to the second chosen angle.

4. The apparatus of claim 3, wherein the first chosen angle and the second chosen angle are between 120° and 150°.

5. The apparatus of claim 3, wherein the portion of the first leg directed out of the planar portion is parallel to the portion of the second leg directed out of the planar portion.

6. The apparatus of claim 5, wherein said first rod forms a third angle with the planar portion, and said second rod makes a fourth angle with the planar portion on the same side of the planar portion as the third angle, the enlarged portion of said first rod being directed toward the enlarged portion of said second rod.

7. The apparatus of claim 6, wherein the third angle is equal to the fourth angle.

8. The apparatus of claim 7, wherein the third angle and the fourth angle are between 35° and 50°.

9. The apparatus of claim 1, wherein the portion of the first leg directed out of the planar portion has a first chosen length and the portion of the second leg directed out of the planar portion has a second chosen length.

10. The apparatus of claim 9, wherein the first chosen length and the second chosen length are equal.

11. The apparatus of claim 1, wherein said first spring has a first chosen spring constant, and said second spring has a second chosen spring constant.

12. The apparatus of claim 11, wherein the first chosen spring constant and the second chosen spring constant are equal.

13. The apparatus of claim 1 wherein said first rod is threaded in the region of the end thereof away from the enlarged portion thereof, and wherein said second rod is threaded in the region of the end thereof away from the enlarged portion thereof.

14. The apparatus of claim 13, further comprising a first nut adapted to be threaded onto the threaded portion of said first rod, and a second nut adapted to be threaded onto the threaded portion of said second rod, whereby said first rod remains in said at least one first hole and said second rod remains in said at least one second hole when said apparatus is not attached to the left ventricle of a heart.

15. The apparatus of claim 1, wherein said apparatus is attached to the left ventricle of a heart in the region of the base of the U-shaped portion, in the region of the portion of the first leg directed out of the planar portion away from the planar portion, and in the region of the portion of the second leg directed out of the planar portion away from the planar portion.

16. The apparatus of claim 1, wherein said first spring and said second spring are coated to prevent growth of tissue thereon.

17. The apparatus of claim 1, wherein the region of the portion of the first leg directed out of the planar portion away from the planar portion, and the region of the portion of the second leg directed out of the planar portion away from the planar portion are enlarged to reduce puncturing of the heart.

18. The apparatus of claim 1, further including a first spacer adapted to fit onto said first rod between said first spring and said first leg, and a second spacer adapted to fit onto said second rod between said second spring and said second leg, whereby the spring-loading of said first rod and the spring loading of said second rod can be adjusted.

* * * * *